United States Patent [19]

Smith et al.

[11] Plant 4,393

[45] Mar. 6, 1979

[54] CHRYSANTHEMUM PLANT NAMED CRIMSON ANNE

[75] Inventors: Edward A. Smith, Walberton; Keith D. Butters, Littlehampton, both of England

[73] Assignee: Pan American Plant Company, West Chicago, Ill.

[21] Appl. No.: 899,726

[22] Filed: Apr. 24, 1978

[51] Int. Cl.[2] ..... A01H 5/00

[52] U.S. Cl. ..... Plt./82

[58] Field of Search ..... Plt./82, 79

*Primary Examiner*—Robert E. Bagwill

*Attorney, Agent, or Firm*—Chas. W. Rummler

[57] ABSTRACT

A new variety of *Chrysanthemum morifolium* for greenhouse pot plant culture originated in England as a natural sport of Red Anne (unpatented) and distinguished by the much deeper red coloration of its blooms when compared to those of Red Anne. Otherwise the physiological characteristics of the new plant are very similar to those of its parent and the new plant enjoys the same advantages of growth, plant size and photoperiod response as the parent.

1 Drawing Figure

BACKGROUND OF THE NEW PLANT

This chrysanthemum cultivar was discovered by Edward A. Smith in 1972 in his greenhouse facilities at Walberton, Sussex, England, as a natural sport of the variety Red Anne. Because of its deeper and very attractive red color, this sport was promptly selected for propagation and testing, which was done by Keith D. Butters at nurseries in Littlehampton, Sussex, England, by means of cuttings from the original plant supplied by Mr. Smith, the discoverer. Propagation of this new plant through successive generations at Littlehampton demonstrated that the novel characteristics of the cultivar held true from generation to generation and appeared to be firmly fixed and as a result, this new chrysanthemum variety was introduced to the European market in 1974. Subsequently, plant material was sent to West Chicago, Ill., for test and evaluation for the American market. Successful test of this new cultivar has led to the propagation of the plant on a commercial scale, by means of vegetative cuttings, at West Chicago, Ill., and at Cortez, Fla., for introduction to the American market.

DESCRIPTION OF THE DRAWINGS

Our new chrysanthemum cultivar is illustrated by the accompanying drawings, of which sheet one is a full color photographic rendition of two views, the upper view showing a display of an entire plant and the lower view showing a full face view of the blossom of the new plant at the left and a similar view of the parent plant bloom at the right. These photographs were made at West Chicago, Ill., in November 1977 and the color reproduction is as nearly true as it is reasonably possible to be had by conventional professional photographic and photo-finishing procedures.

Sheet two of the drawings is a reproduction of a photocopy of typical leaves of the new plant at various stages of maturity.

DESCRIPTION OF THE NEW PLANT

The following is a detailed description of our new chrysanthemum plant according to observations made in November 1977 at West Chicago, Ill., the color designations being according to the R.H.S. Colour Chart published by The Royal Horticultural Society of London, England.

THE PLANT

Origin: A natural sport.

Parentage: Red Anne (unpatented).

Classification:

*Botanic.*—*Chrysanthemum morifolium.*

*Commercial.*—Greenhouse pot chrysanthemum.

Form: Upright perennial herbaceous bush.

Growth: Vigorous and sturdy with very good strength and normal branching under natural conditions.

Foliage:

*Quantity.*—Abundant, 3 to 5 leaves per 10 cm. of stem length.

*Size of leaf.*—About 7.5 to 13.6 cm. long and 5.4 to 10.6 cm. wide.

*Shape of leaf.*—Lobed lanceolate with slightly serrated margins.

*Surface texture.*—Canescent.

*Venation.*—Pinnate.

*Color.*—Upper side — RHS 147A. Under side — RHS 147B.

*Petioles.*—About 1.4 to 2.1 cm. long.

THE BUD

Form: Elliptical.

Size: About 1.3 to 1.6 cm. in diameter and about 7 mm. to 10 mm. long.

Opening Rate: Slow.

Color when phyllaries first divide: RHS 154A.

Color when florets begin to unfurl: RHS 183B.

Phyllaries: The receptacle bears many involucral, upstanding and spear-shaped bracts on its outside.

*Surface texture.*—Pubescent.

*Color.*—Inside — RHS 147A. Outside — RHS 146A.

Peduncle: Length — About 1.5 to 5.0 cm.

*Strength.*—Upright and strong.

*Surface texture.*—Pubescent.

THE FLOWER

Flowering: Year around with photoperiod control.

*Natural season.*—November 6 to November 14.

*Recommended flowering.*—October through Mid-April.

Blooms:

*Borne.*—A head of many florets borne on a single receptacle.

*Size.*—Large. Diameter: About 8 to 11.5 cm. Depth: About 2.5 to 5.0 cm.

*Shape.*—Cup-shaped when bloom first opens changing later to a generally flat shape.

Flower type: Decorative — composite.

*Florets.*—Number — Numerous.

| Color: | | March | November | December |
|---|---|---|---|---|
| Outer Florets - | Upper | 180B | 180B–179A | 179A |
| | Reverse | 179C | 197C | 182D |
| Inner Florets - | Upper | 46A | 46A | 46A |
| | Reverse | 178B | 178C–178D | 176C |
| Tonality at a distance of 2 meters - 179A | | | | |

*Firmness.*—Medium.

*Appearance.*—Very slight shine.

Peduncle: Length — About 1.5 to 5.0 cm.

*Sturdiness.*—Upright — Strong.

*Color.*—147B-147C.

Persistence: Florets hang on and dry.

Effect of weather: Recommended for greenhouse culture only.

Discoloration after full bloom: Considerable depending upon time of the year.

Fragrance: Typical chrysanthemum.

Lasting quality:

*On plant.*—3 to 5 weeks.

*As cut flower.*—Not recommended.

REPRODUCTIVE ORGANS

Stamens:

*Anthers.*—5 syngenesious stamens.

*Filaments.*—Length — About 10 to 30 mm.

*Color.*—Light yellow.

*Pollen.*—Color — Yellow.

Pistils: Number — One to each ray and disc floret.

*Styles.*—Length — About 3 to 5 mm.

*Stigmas.*—Color — Yellow.

Ovaries: Inferior bicarpellate.

This new chrysanthemum cultivar is mainly of the same general and physiological characteristics as are found in the parent plant, differing in particular by the much deeper red coloration of the flowers. For example, a color comparison of the new cultivar Crimson Anne and its parent Red Anne, flowered in November, is as follows:

| | Crimson Anne | Red Anne |
|---|---|---|
| Outer Florets: | | |
| Upper: | 180B–179A | 178D |
| Reverse: | 179C–180D | 173C–173D |
| Inside Florets: | | |
| Upper: | 46A | 34A–34B |
| Reverse: | 178C–178D | 172D |
| Tonality at 2 Meters: | 179A | 178D |

I claim:

1. A new and distinctive chrysanthemum cultivar, substantially as herein shown and described, distinguished particularly by the deep red coloration of its blooms as compared with its parent variety Red Anne.

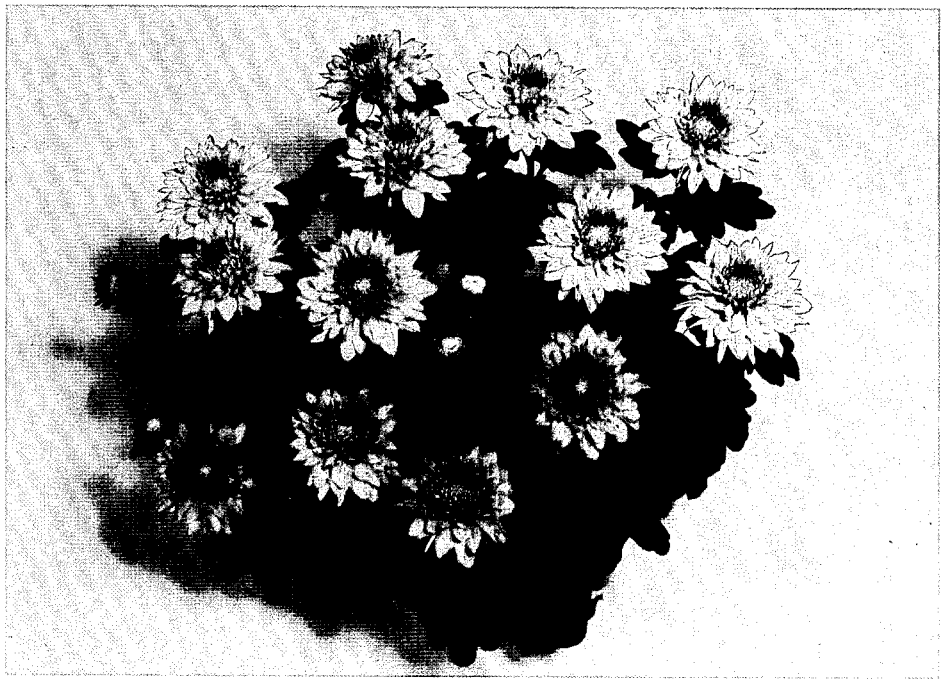
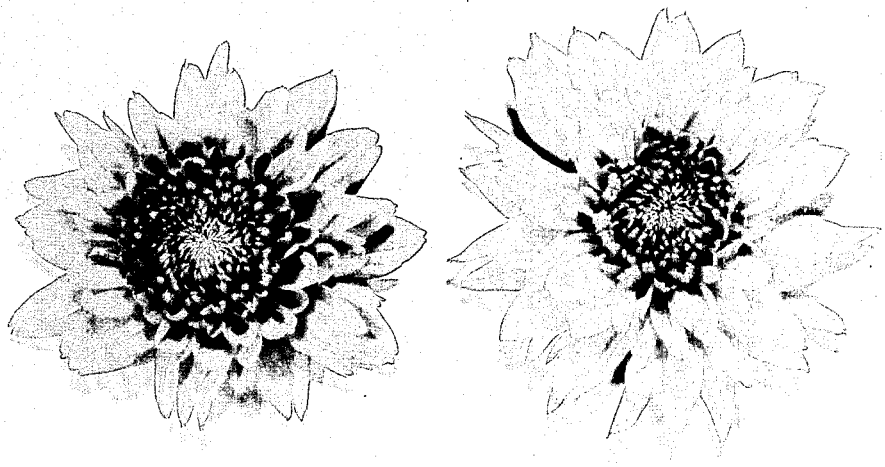

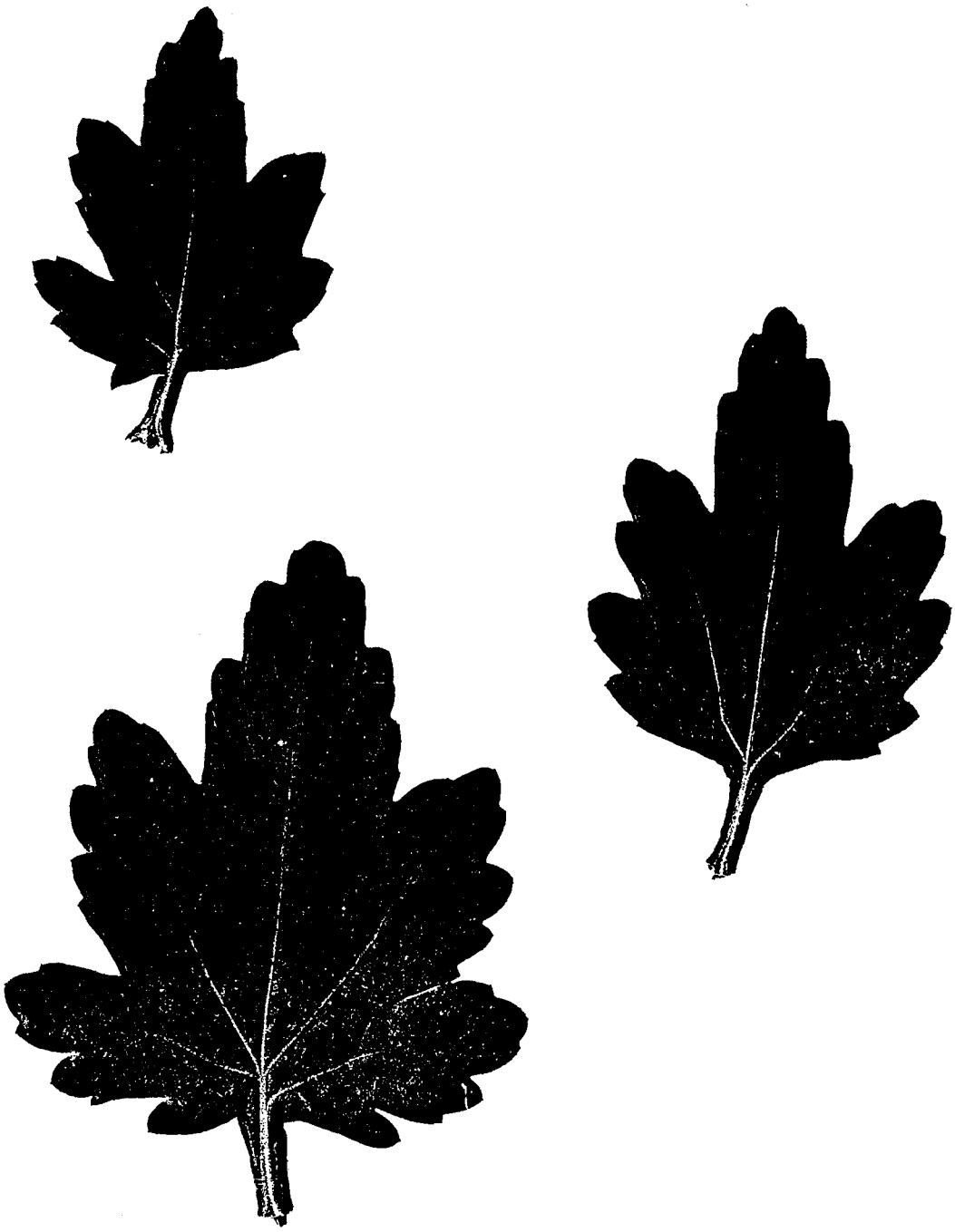

* * * * *